| United States Patent [19] | [11] Patent Number: 5,614,191 |
|---|---|
| Puri et al. | [45] Date of Patent: Mar. 25, 1997 |

[54] IL-13 RECEPTOR SPECIFIC CHIMERIC PROTEINS AND USES THEREOF

[75] Inventors: Raj K. Puri, North Potomac, Md.; Waldemar Debinski, Hummelstown, Pa.; Ira Pastan, Potomac; Nicholas Obiri, Gaithersburg, both of Md.

[73] Assignee: The United States of America as represented by the Department of Health and Human Services, Washington, D.C.

[21] Appl. No.: 404,685

[22] Filed: Mar. 15, 1995

[51] Int. Cl.$^6$ .................. A61K 39/395; C07K 16/46; G01N 33/53

[52] U.S. Cl. .................. 424/178.1; 434/134.1; 434/138.1; 434/183.1; 435/7.23; 435/69.6; 530/387.3; 530/387.7; 530/391.3; 530/391.7

[58] Field of Search .................. 424/134.1, 143.1, 424/138.1, 155.1, 172.1, 173.1, 178.1, 174.1, 183.1, 7.23; 435/69.6, 69.7, 91.4, 188, 240.37, 252.33; 530/387.3, 387.7, 388.8, 389.7, 391.7, 391.3

[56] References Cited

U.S. PATENT DOCUMENTS 5,082,927  1/1992  Pastan et al. .................. 530/351

FOREIGN PATENT DOCUMENTS

WO94/04680  of 0000  WIPO.

OTHER PUBLICATIONS

Thrush et al 1996 Ann Rev Immunol vol. 14 49–71.
Obiri et al. (1995). J. Biol. Chem vol. 270, No. 15:8797.
Debinski et al. (1993) J. Biol. Chem vol. 268 No. 19:14065.
Debinski et al. (1994). Bioconjugate Chem vol. 5:40–46.
Chester et al (1995) Tibtech vol. 13:294–300.
Gottstein et al (1994) Annab of Oncology vol. 5 Supplement 1: S97–103.
Vita et al., *Journ. of Biol. Chem.*, 270:3512 (1995).
Chaudhary et al., *Nature*, 339: 394–397 (1989).
McKenzie et al. *Proc. Natl. Acad. Sci. USA*, 90: 3735 (1993).
Pastan et al., *Ann. Rev. Biochem.*, 61: 331–354 (1992).
Minty et al., *Nature*, 362: 248 (1993).

*Primary Examiner*—Christine M. Nucker
*Assistant Examiner*—Julie E. Reeves
*Attorney, Agent, or Firm*—Townsend and Townsend and Crew LLP

[57] ABSTRACT

The present invention provides a method and compositions for specifically delivering an effector molecule to a tumor cell. The method involves providing a chimeric molecule that comprises an effector molecule attached to a targeting molecule that specifically binds an IL-13 receptor and contacting a tumor cell with the chimeric molecule.

21 Claims, No Drawings

IL-13 RECEPTOR SPECIFIC CHIMERIC PROTEINS AND USES THEREOF

FIELD OF THE INVENTION

This invention relates to methods of specifically delivering an effector molecule to a tumor cell. In particular this invention relates to chimeric molecules that specifically bind to IL-13 receptors and their use to deliver molecules having a particular activity to tumors overexpressing IL-13 receptors.

BACKGROUND OF THE INVENTION

In a chimeric molecule, two or more molecules that exist separately in their native state are joined together to form a single molecule having the desired functionality of all of its constituent molecules. Frequently, one of the constituent molecules of a chimeric molecule is a "targeting molecule". The targeting molecule is a molecule such as a ligand or an antibody that specifically binds to its corresponding target, for example a receptor on a cell surface. Thus, for example, where the targeting molecule is an antibody, the chimeric molecule will specifically bind (target) cells and tissues beating the epitope to which the antibody is directed.

Another constituent of the chimeric molecule may be an "effector molecule". The effector molecule refers to a molecule that is to be specifically transported to the target to which the chimeric molecule is specifically directed. The effector molecule typically has a characteristic activity that is desired to be delivered to the target cell. Effector molecules include cytotoxins, labels, radionuclides, ligands, antibodies, drugs, liposomes, and the like.

In particular, where first effector molecule is a cytotoxin, the chimeric molecule may act as a potent cell-killing agent specifically targeting the cytotoxin to cells bearing a particular target molecule. For example, chimeric fusion proteins which include interleukin 4 (IL-4) or transforming growth factor (TGFcα) fused to Pseudomonas exotoxin (PE) or interleukin 2 (IL-2) fused to Diphtheria toxin (DT) have been shown to specifically target and kill cancer cells (Pastan et al., Ann. Rev. Biochem., 61: 331–354 (1992)).

Generally, it is desirable to increase specificity and affinity and decrease cross-reactivity of the chimeric cytotoxins in order to increase their efficacy. To the extent the chimeric molecule preferentially selects and binds to its target (e.g. a tumor cell) and not to a non-target (e.g. a healthy cell), side effects of the chimeric molecule will be minimized. Unfortunately, many targets to which chimeric molecules have been directed (e.g. the IL-2 and IL-4 receptors), while showing elevated expression on tumor cells, are also expressed at significant levels on healthy cells. Thus, chimeric molecules directed to these targets (e.g. cytotoxins) show some adverse side-effects as they bind non-target cells that also express the targeted receptor.

SUMMARY OF THE INVENTION

The present invention provides methods and compositions for specifically delivering an effector molecule to a tumor cell. In particular, the present invention provides chimetic molecules that specifically target tumor cells with less binding to healthy cells than other analogous chimeric molecules known in the prior art.

The improved specific targeting of this invention is premised, in part, on the discovery that tumor cells, especially carcinomas such as renal cell carcinoma, overexpress IL-13 receptors at extremely high levels. The extremely high level of IL-13 receptor expression on target tumor cells permits the use of lower dosages of chimeric molecule to deliver the same amount of effector molecule to the target cells and also results in reduced binding of non-tumor cells.

In a preferred embodiment, this invention provides for a method for specifically delivering an effector molecule to a tumor cell bearing an IL-13 receptor. The method involves providing a chimeric molecule comprising an effector molecule attached to a targeting molecule that specifically binds to an IL-13 receptor and contacting the tumor with the chimeric molecule resulting in binding of the chimeric molecule to the tumor cell.

The targeting molecule is preferably either a ligand, such as IL-13, that specifically binds an IL-13 receptor or an anti-IL-13 receptor antibody. The targeting molecule may be conjugated to the effector molecule, or where both targeting and effector molecules are polypeptides, the targeting molecule may be joined to the effector molecule through one or more peptide bonds thereby forming a fusion protein. Suitable effector molecules include a cytotoxin, a label, a radionuclide, a drug, a liposome, a ligand, and an antibody. In a particularly preferred embodiment, the effector is a cytotoxin, more specifically a Pseudomonas exotoxin such as PE38QQR. Where the Pseudomonas exotoxin is fused to an IL-13 targeting molecule, a preferred fusion protein is IL-13-PE38QQR.

In another embodiment, this invention provides a method for impairing the growth of tumor cells, more preferably solid tumor cells, bearing an IL-13 receptor. The method involves contacting the tumor with a chimeric molecule comprising an effector molecule selected from the group consisting of a cytotoxin, a radionuclide, a ligand and an antibody; said effector molecule being attached to a targeting molecule that specifically binds a human IL-13 receptor. The targeting molecule is preferably a ligand (such as IL-13) that binds the IL-13 receptor or an anti-IL-13 receptor antibody. Preferred cytotoxic effector molecules include Pseudomonas exotoxin, Diphtheria toxin, ricin and abrin. Psuedomonas exotoxins, such as PE38QQR, are particularly preferred. The targeting molecule may be conjugated or fused to the effector molecule with attachment by fusion preferred for cytotoxic effector molecules. The tumor growth that is impaired may be tumor growth in a human. Thus the method may further comprise administering the chimeric molecule to a human intravenously into a body cavity, or into a human or an organ.

In yet another embodiment, this invention provides for a method of detecting the presence or absence of a tumor. The method involves contacting the tumor with a chimetic molecule comprising a detectable label attached to a targeting molecule that specifically binds a human IL-13 receptor and detecting the presence or absence of the label. In a preferred embodiment, the label is selected from the group consisting of a radioactive label, an enzymatic label, an electron dense label, and a fluorescent label.

This invention also provides for vectors comprising a nucleic acid sequence encoding a chimefie polypeptide fusion protein comprising an IL-13 attached to a second polypeptide. The chimetic polypeptide fusion protein specifically binds to a tumor cell beating an IL-13 receptor. A preferred vector encodes an IL-13-PE fusion protein and more preferably encodes an IL-13-PE38QQR fusion protein.

This invention also provides for host cells comprising a nucleic acid sequence encoding a chimeric polypeptide fusion protein comprising an IL-13 attached to a second polypeptide. A preferred host cell comprises a nucleic acid encoding an IL-13-PE fusion protein, more preferably encoding an IL-13-PE38QQR fusion protein. The encoded fusion protein specifically binds to a tumor cell bearing an IL-13 receptor. Particularly preferred host cells are bacterial host cells, especially E. coli cells.

In still yet another embodiment, this invention provides chimeric molecules that specifically bind a tumor cell bearing an IL-13 receptor. In one preferred embodiment, the chimeric molecule comprises a cytotoxic molecule attached to a targeting molecule that specifically binds an IL-13. The targeting molecule may be conjugated or fused to the cytotoxic molecule. In a preferred embodiment, the targeting molecule is fused to the cytotoxin thereby forming a single-chain fusion protein. Particularly preferred targeting molecules are IL-13 or an antibody that specifically binds to the IL-13 receptor. Preferred cytotoxic molecules include Pseudomonas exotoxin, Diphtheria toxin, ricin, and abrin, with Pseudomonas exotoxins (especially PE38QQR) being most preferred.

In another preferred embodiment, the chimeric molecule comprises an effector molecule attached to an antibody that specifically binds to an IL-13 receptor. Effector molecules include a cytotoxin, a label, a radionuclide, a drug, liposome, a ligand and an antibody. The effector molecule may be fused or conjugated to the antibody.

The invention additionally provides for pharmacological compositions comprising a pharmaceutically acceptable carrier and a chimeric molecule where the chimeric molecule comprises and effector molecule attached to a targeting molecule that specifically binds to an IL-13 receptor. The targeting and effector molecules may be conjugated or fused to each other. Particularly preferred targeting molecules include IL-13 and anti-IL-13 receptor antibodies, while preferred effector molecules include a cytotoxin, a label, a radionuclide, a drug, a liposome, a ligand and an antibody. A preferred pharmacological composition includes an IL-13-PE fusion protein, more preferably an IL-13-PE38QQR fusion protein.

Definitions

The term "specifically deliver" as used herein refers to the preferential association of a molecule with a cell or tissue beating a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule. Specific delivery typically results in greater than 2 fold, preferably greater than 5 fold, more preferably greater than 10 fold and most preferably greater than 100 fold increase in amount of delivered molecule (per unit time) to a cell or tissue bearing the target molecule as compared to a cell or tissue lacking the target molecule or marker.

The term "residue" as used herein refers to an amino acid that is incorporated into a polypeptide. The amino acid may be a naturally occurring amino acid and, unless otherwise limited, may encompass known analogs of natural amino acids that can function in a similar manner as naturally occurring amino acids.

A "fusion protein" refers to a polypeptide formed by the joining of two or more polypeptides through a peptide bond formed between the amino terminus of one polypeptide and the carboxyl terminus of another polypeptide. The fusion protein may be formed by the chemical coupling of the constituent polypeptides or it may be expressed as a single polypeptide from nucleic acid sequence encoding the single contiguous fusion protein. A single chain fusion protein is a fusion protein having a single contiguous polypeptide backbone.

A "spacer" as used herein refers to a peptide that joins the proteins comprising a fusion protein. Generally a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

A "ligand", as used herein, refers generally to all molecules capable of reacting with or otherwise recognizing or binding to a receptor on a target cell. Specifically, examples of ligands include, but are not limited to, antibodies, lymphokines, cytokines, receptor proteins such as CD4 and CD8, solubilized receptor proteins such as soluble CD4, hormones, growth factors, and the like which specifically bind desired target cells.

DETAILED DESCRIPTION

Chimeric Molecules Targeted to the IL-13 Receptor

The present invention provides a method for specifically delivering an effector molecule to a tumor cell. This method involves the use of chimeric molecules comprising a targeting molecule attached to an effector molecule. The chimeric molecules specifically target tumor cells while providing reduced binding to non-target cells as compared to other targeted chimeric molecules known in the art.

The improved specific targeting of this invention is premised, in part, on the discovery that solid tumors, especially carcinomas, overexpress IL-13 receptors at extremely high levels. While the IL-13 receptors are overexpressed on tumor cells, expression on other cells (e.g. monocytes and T cells) appears negligible. Thus, by specifically targeting the IL-13 receptor, the present invention provides chimeric molecules that are specifically directed to solid tumors while minimizing targeting of other cells or tissues.

In a preferred embodiment, this invention provides for compositions and methods for impairing the growth of tumors. The methods involve providing a chimeric molecule comprising a cytotoxic effector molecule attached to a targeting molecule that specifically binds an IL-13 receptor. The cytotoxin may be a native or modified cytotoxin such as Pseudomonas exotoxin (PE), Diphtheria toxin (DT), ricin, abrin, and the like.

The chimeric cytotoxin is administered to an organism containing tumor cells which are then contacted by the chimeric molecule. The targeting molecule component of the chimeric molecule specifically binds to the overexpressed IL-13 receptors on the tumor cells. Once bound to the IL-13 receptor on the cell surface, the cytotoxic effector molecule mediates internalization into the cell where the cytotoxin inhibits cellular growth or kills the cell.

The use of chimeric molecules comprising a targeting moiety joined to a cytotoxic effector molecules to target and kill tumor cells is known in the prior art. For example, chimeric fusion proteins which include interleukin 4 (IL-4) or transforming growth factor (TGFα) fused to Pseudomonas exotoxin (PE) or interleukin 2 (IL-2) fused to Diphtheria toxin (DT) have been tested for their ability to specifically target and kill cancer cells (Pastan et al., *Ann. Rev. Biochem.*, 61: 331–354 (1992)).

Although chimeric IL-4-cytotoxin molecules are known in the prior art, and IL-4 shows some sequence similarity to IL-13, it was an unexpected discovery of the present invention that cytotoxins targeted by a moiety specific to the IL-13 receptor show significantly increased efficacy as compared to IL-4 receptor directed cytotoxins. Without being bound to a particular theory, it is believed that the improved efficacy of the IL-13 chimeras of the present invention is due to at least three factors.

First, IL-13 receptors are expressed at much lower levels, if at all on non-tumor cells (e.g. monocytes, T cells, B cells). Thus cytotoxins directed to IL-13 receptors show reduced binding and subsequent killing of healthy cells and tissues as compared to cytotoxins directed to IL-4 receptors.

Second, the receptor component that specifically binds IL-13 appears to be expressed at significantly higher levels on solid tumors than the receptor component that binds IL-4. Thus, tumor cells bind higher levels of cytotoxic chimeric molecules directed against IL-13 receptors than cytotoxic chimeric molecules directed against IL-4 receptors.

Finally, IL-4 receptors are up-regulated when immune system cells (e.g. T-cells) are activated. This results in healthy cells, for example T-cells and B-cells, showing greater susceptibility to IL-4 receptor directed cytotoxins. Thus, the induction of an immune response (as against a cancer), results in greater susceptiblity of cells of the immune system to the therapeutic agent. In contrast, IL-13 receptors are not up-regulated in activated cells. Thus IL-13 receptor targeted cytotoxins have no greater effect on activated cells and thereby minimize adverse effects of the therapeutic composition on cells of the immune system.

In another embodiment, this invention also provides for compositions and methods for detecting the presence or absence of tumor cells. These methods involve providing a chimeric molecule comprising an effector molecule, that is a detectable label attached to a targeting molecule that specifically binds an IL-13 receptor. The IL-13 receptor targeting moiety specifically binds the chimetic molecule to tumor cells which are then marked by their association with the detectable label. Subsequent detection of the cell-associated label indicates the presence of a tumor cell.

In yet another embodiment, the effector molecule may be another specific binding moiety such as an antibody, a growth factor, or a ligand. The chimetic molecule will then act as a highly specific bifunctional linker. This linker may act to bind and enhance the interaction between cells or cellular components to which the fusion protein binds. Thus, for example, where the "targeting" component of the chimefie molecule comprises a polypeptide that specifically binds to an IL-13 receptor and the "effector" component is an antibody or antibody fragment (e.g. an Fv fragment of an antibody), the targeting component specifically binds cancer cells, while the effector component binds receptors (e.g., IL-2 or IL-4 receptors) on the surface of immune cells. The chimeric molecule may thus act to enhance and direct an immune response toward target cancer cells.

In still yet another embodiment the effector molecule may be a pharmacological agent (e.g. a drug) or a vehicle containing a pharmacological agent. This is particularly suitable where it is merely desired to invoke a non-lethal biological response. Thus the moiety that specifically binds to an IL-13 receptor may be conjugated to a drug such as vinblastine, doxirubicin, genistein (a tyrosine kinase inhibitor), an antisense molecule, and other pharmacological agents known to those of skill in the art, thereby specifically targeting the pharmacological agent to tumor cells over expressing IL-13 receptors.

Alternatively, the targeting molecule may be bound to a vehicle containing the therapeutic composition. Such vehicles include, but are not limited to liposomes, micelles, various synthetic beads, and the like.

One of skill in the art will appreciate that the chimeric molecules of the present invention may include multiple targeting moieties bound to a single effector or conversely, multiple effector molecules bound to a single targeting moiety. In still other embodiment, the chimeric molecules may include both multiple targeting moieties and multiple effector molecules. Thus, for example, this invention provides for "dual targeted" cytotoxic chimeric molecules in which targeting molecule that specifically binds to IL-13 is attached to a cytotoxic molecule and another molecule (e.g. an antibody, or another ligand) is attached to the other terminus of the toxin. Such a dual-targeted cytotoxin might comprise an IL-13 substituted for domain Ia at the amino terminus of a PE and anti-TAC(fv) inserted in domain III, between amino acid 604 and 609. Other antibodies may also be suitable.

The Targeting Molecule

In a preferred embodiment, the targeting molecule is a molecule that specifically binds to the IL-13 receptor. The term "specifically binds", as used herein, when referring to a protein or polypeptide, refers to a binding reaction which is determinative of the presence of the protein or polypeptide in a heterogeneous population of proteins and other biologics. Thus, under designated conditions (e.g. immunoassay conditions in the case of an antibody), the specified ligand or antibody binds to its particular "target" protein (e.g. an IL-13 receptor protein) and does not bind in a significant amount to other proteins present in the sample or to other proteins to which the ligand or antibody may come in contact in an organism.

A variety of immunoassay formats may be used to select antibodies specifically immunoreactive with an IL-13 receptor protein. For example, solid-phase ELISA immunoassays are routinely used to select monoclonal antibodies specifically immunoreactive with a protein. See Harlow and Lane (1988) Antibodies, A Laboratory Manual, Cold Spring Harbor Publications, New York, for a description of immunoassay formats and conditions that can be used to determine specific immunoreactivity.

Similarly, assay formats for detecting specific binding of ligands (e.g. IL-13) with their respective receptor are also well known in the art. Example 1 provides a detailed protocol for assessing specific binding of labeled IL-13 by and IL-13 receptor.

The IL-13 receptor is a cell surface receptor that specifically binds IL-13 and mediates a variety of physiological responses in various cell types as described below in the description of IL-13. The IL-13 receptor may be identified by contacting a cell or other sample with labeled IL-13 and detecting the amount of specific binding of IL-13 according to methods well known to those of skill in the art. Detection of IL-13 receptors by labeled IL-13 binding is described in detail in Example 1.

Alternatively, an anti-IL-13 receptor antibody may also be used to identify IL-13 receptors. The antibody will specifically bind to the IL-13 receptor and this binding may be detected either through detection of a conjugated label or through detection of a labeled second antibody that binds the anti-IL-13 receptor antibody.

In a preferred embodiment, the moiety utilized to specifically target the IL-13 receptor is either an antibody that specifically binds the IL-13 receptor (an anti-IL-13R antibody) or a ligand, such as IL-13, that specifically binds to the receptor.

IL-13

IL-13 is a pleiotropic cytokine that is recognized to share many of the properties of IL-4. IL-13 has approximately 30% sequence identity with IL-4 and exhibits IL-4-like activities on monocytes/macrophages and human B cells (Minty et al., *Nature*, 362: 248 (1993), McKenzie et al. *Proc. Natl. Acad. Sci. USA*, 90: 3735 (1987)). In particular, IL-13 appears to be a potent regulator of inflammatory and immune responses. Like IL-4, IL-13 can up-regulate the monocyte/macrophage expression of CD23 and MHC class I and class II antigens, down-regulate the expression of Fcγ, and inhibit antibody-dependent cytotoxicity. IL-13 can also inhibit nitric oxide production as well as the expression of pro-inflammatory cytokines (e.g. IL-1, IL-6, IL-8, IL-10 and IL-12) and chemokines (MIP-1, MCP), but enhance the production of IL-1ra (Minty supra.; Mckenzie et al., supra.; Zurawski et al. *Immunol. Today*, 15: 19 (1994); de Wall Malefyt et al. *J. Immunol.*, 150: 180A (1993); de Wall Malefyt et al. *J. Immunol.*, 151: 6370 (1993); Doherty et al. *J. Immunol.*, 151: 7151 (1993); and Minty et al. *Eur. cytokine Netw.*, 4: 99 (1993)).

Recombinant IL-13 is commercially available from a number of sources (see, e.g. R & D Systems, Minneapolis, Minn., U.S.A., and Sanoff Bio-Industries, Inc., Tervose, Pa., U.S.A.). Alternatively, a gene or a cDNA encoding IL-13 may be cloned into a plasmid or other expression vector and expressed in any of a number of expression systems according to methods well known to those of skill in the art. Methods of cloning and expressing IL-13 and the nucleic acid sequence for IL-13 are well kown (see, for example, Minty et al. (1993) supra. and McKenzie (1987), supra). In addition, the expression of IL-13 as a component of a chimeric molecule is detailed in Example 4.

One of skill in the art will appreciate that analogues or fragments of IL-13 bearing will also specifically bind to the IL-13 receptor. For example, conservative substitutions of residues (e.g., a serine for an alaninc or an aspartic acid for a glutamic acid) comprising native IL-13 will provide IL-13 analogues that also specifically bind to the IL-13 receptor. Thus, the term "IL-13", when used in reference to a targeting molecule, also includes fragments, analogues or peptide mimetics of IL-13 that also specifically bind to the IL-13 receptor.

Anti-IL-13 Receptor Antibodies

One of skill will recognize that other molecules besides IL-13 will specifically bind to IL-13 receptors. Polyclonal and monoclonal antibodies directed against IL-13 receptors provide particularly suitable targeting molecules in the chimeric molecules of this invention. The term "antibody", as used herein, includes various forms of modified or altered antibodies, such as an intact immunoglobulin, various fragments such as an Fv fragment, an Fv fragment containing only the light and heavy chain variable regions, an Fv fragment linked by a disulfide bond (Brinkmann, et al. *Proc. Natl. Acad. Sci. USA*, 90: 547–551 (1993)), an Fab or (Fab)'₂ fragment containing the variable regions and parts of the constant regions, a single-chain antibody and the like (Bird et al., *Science* 242: 424–426 (1988); Huston et al., *Proc. Nat. Acad. Sci. USA* 85: 5879–5883 (1988)). The antibody may be of animal (especially mouse or rat) or human origin or may be chimeric (Morrison et al., *Proc Nat. Acad. Sci. USA* 81: 6851–6855 (1984)) or humanized (Jones et al., *Nature* 321: 522–525 (1986), and published UK patent application #8707252). Methods of producing antibodies suitable for use in the present invention are well known to those skilled in the art and can be found described in such publications as Harlow & Lane, *Antibodies: A Laboratory Manual*, Cold Spring Harbor Laboratory (1988), and Asai, Methods in Cell Biology Vol. 37: *Antibodies in Cell Biology*, Academic Press, Inc. New York (1993).

Antibodies that specifically bind the IL-13 receptor may be produced by a number of means well known to those of skill in the art. Generally, this involves using an antigenic component of the IL-13 receptor as an antigen to induce the production of antibodies in an organism (e.g. a sheep, mouse, rabbit, etc.). One of skill in the art will recognize that there are numerous methods of isolating all or components of the IL-13 receptor for use as an antigen. For example, IL-13 receptors may be isolated by crosslinking the receptor to a labeled IL-13 by the exposure to 2 mM disuccinimidyl subcrate (DSS). The labeled receptor may then be isolated according to routine methods and the isolated receptor may be used as an antigen to raise anti-IL-13 receptor antibodies as described below. Cross-linking and isolation of components of the IL-13 receptor is described in Example 3.

In a preferred embodiment, however, IL-13 receptors may be isolated by means of affinity chromatography. It was a surprising discovery of the present invention that solid tumor cells overexpress IL-13 receptors. This discovery of cells overexpressing IL-13 receptor greatly simplifies the receptor isolation. Generally, approximately, 100 million renal carcinoma cells, may be solubilized in detergent with protease inhibitors according to standard methods. The resulting lysate is then run through an affinity column bearing IL-13. The receptor binds to the IL-13 in the column thereby effecting an isolation from the lysate. The column is then eluted with a low pH buffer to dissociate the IL-13 ligand from the IL-13 receptor resulting in isolated receptor. The isolated receptor may then be used as an antigen to raise anti-IL-13 receptor antibodies.

Antibody Production

Methods of producing polyclonal antibodies are known to those of skill in the art. In brief, an immunogen, preferably an isolated IL-13 receptor or receptor epitope is mixed with an adjuvant and animals are immunized with the mixture. The animal's immune response to the immunogen preparation is monitored by taking test bleeds and determining the tiler of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired. See, e.g., Coligan (1991) *Current Protocols in Immunology* Wiley/Greene, New York; and Harlow and Lane (1989) *Antibodies: A Laboratory Manual* Cold Spring Harbor Press, New York, which are incorporated herein by reference.

Monoclonal antibodies may be obtained by various techniques familiar to those skilled in the art. Description of techniques for preparing such monoclonal antibodies may be found in, e.g., Stites et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.) Academic Press, New York, N.Y.; and particularly in Kohler and Milstein (1975) *Nature* 256: 495–497, which discusses one method of generating monoclonal antibodies. Summarized briefly, this method involves injecting an animal with an immunogen. The animal is then sacrificed and cells taken from its spleen, which are then fused with myeloma cells (See, Kohler and Milstein (1976) *Eur. J. Immunol.* 6: 511–519, incorporated herein by reference). The result is a hybrid cell or "hybridoma" that is capable of reproducing in vitro.

Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al. (1989) *Science* 246: 1275–1281. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, Huse et al. *Science* 246: 1275–1281 (1989); and Ward, et al. *Nature* 341: 544–546 (1989). In general suitable monoclonal antibodies will usually bind their target epitope with at least a $K_D$ of about 1 mM, more usually at least about 300 µM, and most preferably at least about 0.1 µM or better.

Other Targeting Antibodies

Where the chimeric molecule contains more than one targeting molecule (e.g. a dual-targeted cytotoxin), the molecule may contain targeting antibodies directed to tumor markers other than the overexpressed IL-13 receptor. A number of such antibodies are known and have even been converted to form suitable for incorporation into fusion proteins. These include anti-erbB2, B3, BR96, OVB3, anti-transferrin, Mik-β1 and PR1 (see Batra et at., *Mol. Cell. Biol.*, 11: 2200–2205 (1991); Batra et at., *Proc. Natl. Acad. Sci. USA*, 89: 5867–5871 (1992); Brinkmann, et al. *Proc. Natl. Acad. Sci. USA*, 88: 8616–8620 (1991); Brinkmann et al., *Proc. Natl. Acad. Sci. USA*, 90: 547–551 (1993); Chaudhary et al., *Proc. Natl. Acad. Sci. USA*, 87: 1066–1070 (1990); Friedman et al., *Cancer Res.* 53: 334–339 (1993); Kreitman et al., *J. Immunol.*, 149: 2810–2815 (1992); Nicholls et al., *J. Biol. Chem.*, 268: 5302–5308 (1993); and Wells, et al., *Cancer Res.*, 52: 6310–6317 (1992), respectively).

The Effector Molecule

As described above, the effector molecule component of the chimeric molecules of this invention may be any molecule whose activity it is desired to deliver to cells that overexpress IL-13 receptors. Particularly preferred effector molecules include cytotoxins such as PE or DT, radionuclides, ligands such as growth factors, antibodies, detectable labels such as fluorescent or radioactive labels, and therapeutic compositions such as liposomes and various drugs.

Cytotoxins

Particularly preferred cytotoxins include Pseudomonas exotoxins, Diphtheria toxins, ricin, and abrin. Pseudomonas exotoxin and Dipthteria toxin are most preferred.

Pseudornonas exotoxin (PE)

Pseudomonas exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1–252) mediates cell binding. Domain II (amino acids 253–364) is responsible for translocation into the cytosol and domain III (amino acids 400–613) mediates ADP ribosylation of elongation factor 2, which inactivates the protein and causes cell death. The function of domain Ib (amino acids 365–399) remains undefined, although a large part of it, amino acids 365–380, can be deleted without loss of cytotoxicity. See Siegall et al., *J. Biol. Chem.* 264: 14256–14261 (1989), incorporated by reference herein.

Where the targeting molecule (e.g. IL-13) is fused to PE, a preferred PE molecule is one in which domain Ia (amino acids 1 through 252) is deleted and amino acids 365 to 380 have been deleted from domain Ib. However all of domain Ib and a portion of domain II (amino acids 350 to 394) can be deleted, particularly if the deleted sequences are replaced with a linking peptide such as four glycine residues followed by a serine.

In addition, the PE molecules can be further modified using site-directed mutagenesis or other techniques known in the art, to alter the molecule for a particular desired application. Means to alter the PE molecule in a manner that does not substantially affect the functional advantages provided by the PE molecules described here can also be used and such resulting molecules are intended to be covered herein.

For maximum cytotoxic properties of a preferred PE molecule, several modifications to the molecule are recommended. An appropriate carboxyl terminal sequence to the recombinant molecule is preferred to translocate the molecule into the cytosol of target cells. Amino acid sequences which have been found to be effective include, arginine, followed by EDL and optionally followed by lysine (as in native PE), or DEL preceded by either an arginine or a lysine repeats of those, or other sequences that function to maintain or recycle proteins into the endoplasmic reticulum, referred to here as "endoplasmic retention sequences". See, for example, Chaudhary et al, *Proc. Natl. Acad. Sci. USA* 87: 308–312 and Seetharam et al, *J. Biol. Chem.* 266: 17376–17381 (1991) and commonly assigned, U.S. Ser. No. 07/459,635 filed Jan. 2, 1990, now abandoned, all of which are incorporated by reference herein.

Deletions of amino acids 365–380of domain Ib can be made without loss of activity. Further, a substitution of methionine at amino acid position 280 in place of glycine to allow the synthesis of the protein to begin and of serine at amino acid position 287 in place of cysteine to prevent formation of improper disulfide bonds is beneficial. In a preferred embodiment, the targeting molecule is inserted in replacement for domain Ia. A similar insertion has been accomplished in what is known as the TGFα-PE40 molecule (also referred to as TP40) described in Heimbrook et al., *Proc. Natl. Acad. Sci., USA*, 87: 4697–4701 (1990) and in commonly assigned U.S. Ser. No. 07/865,722filed Apr. 8, 1992 and in U.S. Ser. No. 07/522,563 filed May 14, 1990, now abandonded, all of which are incorporated by reference.

Preferred forms of PE contain amino acids 253–364 and 381–608, and are followed by the native sequences arginine, followed by EDL and further followed by lysine (as in native PE), or the mutant sequences DEL preceded by either an arginine or a lysine. Lysines at positions 590 and 606 may or may not be mutated to glutamine.

In a particularly preferred embodiment, the IL-13 receptor targeted cytotoxins of this invention comprise the PE molecule designated PE38QQR. This PE molecule is a truncated form of PE composed of amino acids 253–364 and 381–608. The lysine residues at positions 509 and 606 are replaced by glutamine and at 613 are replaced by arginine (Debinski et al. *Bioconj. Chem.*, 5: 40 (1994) which is incorporated herein by reference).

The targeting molecule (e.g. IL-13 or anti-IL-13R antibody) may also be inserted at a point within domain III of the PE molecule. Most preferably the targeting molecule is fused between about amino acid positions 607 and 609 of the PE molecule. This means that the targeting molecule is inserted after about amino acid 607 of the molecule and an appropriate carboxyl end of PE is recreated by placing amino acids about 604–613 of PE after the targeting molecule. Thus, the targeting molecule is inserted within the recombinant PE molecule after about amino acid 607 and is followed by amino acids 604–613of domain III. The targeting molecule may also be inserted into domain Ib to replace sequences not necessary for toxicity. Debinski, et al. *Mol. Cell. Biol.*, 11: 1751–1753 (1991).

In a preferred embodiment, the PE molecules will be fused to the targeting molecule by recombinant means. The genes encoding protein chains may be cloned in cDNA or in genomic form by any cloning procedure known to those skilled in the art. See for example Sambrook et al., *Molecular Cloning. A Laboratory Manual*, Cold Spring Harbor Laboratory, (1989), incorporated by reference herein. Methods of cloning genes encoding PE fused to various ligands are well known to those of skill in the art. See, for example, Siegall et al., *FASEB J.*, 3: 2647–2652 (1989); Chaudhary et al. *Proc. Natl. Acad. Sci. USA*, 84: 4538–4542 (1987), which are incorporated herein by reference.

Those skilled in the art will realize that additional modifications, deletions, insertions and the like may be made to the chimeric molecules of the present invention or to the nucleic acid sequences encoding IL-13 receptor-directed chimeric molecules. Especially, deletions or changes may be made in PE or in a linker connecting an antibody gene to PE, in order to increase cytotoxicity of the fusion protein toward target cells or to decrease nonspecific cytotoxicity toward cells without antigen for the antibody. All such constructions may be made by methods of genetic engineering well known to those skilled in the art (see, generally, Sambrook et al., supra) and may produce proteins that have differing properties of affinity, specificity, stability and toxicity that make them particularly suitable for various clinical or biological applications.

Diphtheria TOxin (DT)

Like PE, diphtheria toxin (DT) kills cells by ADP-ribosylating elongation factor 2 thereby inhibiting protein synthesis. Diphtheria toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al., *Science*, 175: 901–903 (1972); Uchida et al. *J. Biol. Chem.*, 248: 3838–3844 (1973)).

In a preferred embodiment, the targeting molecule-Diphtheria toxin fusion proteins of this invention have the native receptor-binding domain removed by truncation of the Diphtheria toxin B chain. Particularly preferred is DT388, a DT in which the carboxyl terminal sequence beginning at residue 389 is removed. Chaudhary, et al., *Bioch. Biophys. Res. Comm.*, 180: 545–551 (1991).

Like the PE chimeric cytotoxins, the DT molecules may be chemically conjugated to the IL-13 receptor targeting molecule, but, in a preferred embodiment, the targeting molecule will be fused to the Diphtheria toxin by recombinant means. The genes encoding protein chains may be cloned in cDNA or in genomic form by any cloning procedure known to those skilled in the art. Methods of cloning genes encoding DT fused to various ligands are also well known to those of skill in the art. See, for example, Williams et al. *J. Biol. Chem.* 265: 11885–11889 (1990) and copending patent application (U.S. Ser. No. 07/620,939) which describe the expression of a number of growth-factor-DT fusion proteins.

The term "Diphtheria toxin" (DT) as used herein refers to full length native DT or to a DT that has been modified. Modifications typically include removal of the targeting domain in the B chain and, more specifically, involve truncations of the carboxyl region of the B chain.

Detectable Labels

Detectable labels suitable for use as the effector molecule component of the chimeric molecules of this invention include any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

Ligands

As explained above, the effector molecule may also be a ligand or an antibody. Particularly preferred ligand and antibodies are those that bind to surface markers of immune cells. Chimetic molecules utilizing such antibodies as effector molecules act as bifunctional linkers establishing an association between the immune cells bearing binding partner for the ligand or antibody and the tumor cells overexpressing the IL-13 receptor. Suitable antibodies and growth factors are known to those of skill in the art and include, but are not limited to, IL-2, IL-4, IL-6, IL-7, tumor necrosis factor (TNF), anti-Tac, TGFα, and the like.

Other Therapeutic Moleties

Other suitable effector molecules include pharmacological agents or encapsulation systems containing various pharmacological agents. Thus, the targeting molecule of the chimeric molecule may be attached directly to a drug that is to be delivered directly to the tumor. Such drugs are well known to those of skill in the art and include, but are not limited to, doxirubicin, vinblastine, genistein, an antisense molecule, and the like.

Alternatively, the effector molecule may be an encapsulation system, such as a liposome or micelie that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735, Connor et al., *Pharm. Ther.*, 28: 341–365 (1985)

Attachment of the Targeting Molecule to the Effector Molecule

One of skill will appreciate that the targeting molecule and effector molecules may be joined together in any order.

Thus, where the targeting molecule is a polypeptide, the effector molecule may be joined to either the amino or carboxy termini of the targeting molecule. The targeting molecule may also be joined to an internal region of the effector molecule, or conversely, the effector molecule may be joined to an internal location of the targeting molecule, as long as the attachment does not interfere with the respective activities of the molecules.

The targeting molecule and the effector molecule may be attached by any of a number of means well known to those of skill in the art. Typically the effector molecule is conjugated, either directly or through a linker (spacer), to the targeting molecule. However, where both the effector molecule and the targeting molecule are polypeptides it is preferable to recombinantly express the chimeric molecule as a single-chain fusion protein.

Conjugation of the Effector Molecule to the Targeting Molecule

In one embodiment, the targeting molecule (e.g. IL-13 or anti-IL-13R antibody) is chemically conjugated to the effector molecule (e.g. a cytotoxin, a label, a ligand, or a drug or liposome). Means of chemically conjugating molecules are well known to those of skill.

The procedure for attaching an agent to an antibody or other polypeptide targeting molecule will vary according to the chemical structure of the agent. Polypeptides typically contain variety of functional groups; e.g., carboxylic acid (COOH) or free amine ($—NH_2$) groups, which are available for reaction with a suitable functional group on an effector molecule to bind the effector thereto.

Alternatively, the targeting molecule and/or effector molecule may be derivatized to expose or attach additional reactive functional groups. The derivatization may involve attachment of any of a number of linker molecules such as those available from Pierce Chemical Company, Rockford Ill.

A "linker", as used herein, is a molecule that is used to join the targeting molecule to the effector molecule. The linker is capable of forming covalent bonds to both the targeting molecule and to the effector molecule. Suitable linkers are well known to those of skill in the art and include, but are not limited to, straight or branched-chain carbon linkers, heterocyclic carbon linkers, or peptide linkers. Where the targeting molecule and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

A bifunctional linker having one functional group reactive with a group on a particular agent, and another group reactive with an antibody, may be used to form the desired immunoconjugate. Alternatively, derivatization may involve chemical treatment of the targeting molecule, e.g., glycol cleavage of the sugar moiety of a the glycoprotein antibody with periodate to generate free aldehyde groups. The free aldehyde groups on the antibody may be reacted with free amine or hydrazine groups on an agent to bind the agent thereto. (See U.S. Pat. No. 4,671,958). Procedures for generation of free sulfhydryl groups on polypeptide, such as antibodies or antibody fragments, are also known (See U.S. Pat. No. 4,659,839).

Many procedure and linker molecules for attachment of various compounds including radionuclide metal chelates, toxins and drugs to proteins such as antibodies are known. See, for example, European Patent Application No. 188,256; U.S. Pat. Nos. 4,671,958, 4,659,839, 4,414,148, 4,699,784; 4,680,338; 4,569,789; and 4,589,071; and Borlinghaus et al. *Cancer Res.* 47: 4071–4075 (1987) which are incorporated herein by reference. In particular, production of various immunotoxins is well-known within the art and can be found, for example in "Monoclonal Antibody-Toxin Conjugates: Aiming the Magic Bullet," Thorpe et al., *Monoclonal Antibodies in Clinical Medicine*, Academic Press, pp. 168–190 (1982), Waldmann, *Science,* 252: 1657 (1991), U.S. Pat. Nos. 4,545,985 and 4,894,443 which are incorporated herein by reference.

In some circumstances, it is desirable to free the effector molecule from the targeting molecule when the chimeric molecule has reached its target site. Therefore, chimeric conjugates comprising linkages which are cleavable in the vicinity of the target site may be used when the effector is to be released at the target site. Cleaving of the linkage to release the agent from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

Production of Fusion Proteins

Where the targeting molecule and/or the effector molecule is relatively short (i.e., less than about 50 amino acids) they may be synthesized using standard chemical peptide synthesis techniques. Where both molecules are relatively short the chimeric molecule may be synthesized as a single contiguous polypeptide. Alternatively the targeting molecule and the effector molecule may be synthesized separately and then fused by condensation of the amino terminus of one molecule with the carboxyl terminus of the other molecule thereby forming a peptide bond. Alternatively, the targeting and effector molecules may each be condensed with one end of a peptide spacer molecule thereby forming a contiguous fusion protein.

Solid phase synthesis in which the C-terminal amino acid of the sequence is attached to an insoluble support followed by sequential addition of the remaining amino acids in the sequence is the preferred method for the chemical synthesis of the polypeptides of this invention. Techniques for solid phase synthesis are described by Barany and Merrifield, *Solid-Phase Peptide Synthesis*; pp. 3–284 in *The Peptides: Analysis, Synthesis, Biology.* Vol. 2: Special Methods in Peptide Synthesis, Part A., Merrifield, et al. *J. Am. Chem. Soc.,* 85: 2149–2156 (1963), and Stewart et al., *Solid Phase Peptide Synthesis,* 2nd ed. Pierce Chem. Co., Rockford, Ill. (1984) which are incorporated herein by reference.

In a preferred embodiment, the chimeric fusion proteins of the present invention are synthesized using recombinant DNA methodology. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins (e.g. IL-13-PE38QQR) of this invention may be prepared by any suitable method, including, for example, cloning and restriction of appropriate sequences or direct chemical synthesis by methods such as the phosphotriester method of Narang et al. *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.*, 22: 1859–1862 (1981); and the solid support method of U.S. Pat. No. 4,458,066, all incorporated by reference herein.

Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Alternatively, subsequences may be cloned and the appropriate subsequences cleaved using appropriate restriction enzymes. The fragments may then be ligated to produce the desired DNA sequence.

In a preferred embodiment, DNA encoding fusion proteins of the present invention may be cloned using DNA amplification methods such as polymerase chain reaction (PCR). Thus, in a preferred embodiment, the gene for IL-13 is PCR amplified, using a sense primer containing the restriction site for NdeI and an antisense primer containing the restriction site for HindIII. In a particularly preferred embodiment, the primers are selected to amplify the nucleic acid starting at position 19, as described by McKenzie et al. (1987), supra. This produces a nucleic acid encoding the mature IL-13 sequence and having terminal restriction sites. A PE38QQR fragment may be cut out of the plasmid pWDMH4-38QQR or plasmid pSGC242FdN1 described by Debinski et al. *Int. J. Cancer,* 58: 744–748 (1994), and by Debinski et al. *Clin. Res.,* 42: 251A (abstract (1994) respectively. Ligation of the IL-13 and PE38QQR sequences and insertion into a vector produces a vector encoding IL-13 joined to the amino terminus of PE38QQR (position 253 of PE). The two molecues are joined by a three amino acid junction consaisting of glutamic acid, alanine, and phenylalanine introduced by the restriction site.

While the two molecules are preferrably essentially directly joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins may be expressed in a variety of host cells, including *E. coli,* other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes, *Protein Purification*, Springer-Verlag, New York (1982), Deutscher, *Methods in Enzymology Vol. 182: Guide to Protein Purification.*, Academic Press, Inc. New York (1990)). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the IL-13 receptor targeted fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art. (See Debinski et al. *J. Biol. Chem.,* 268: 14065–14070 (1993); Kreitman and Pastan, *Bioconjug. Chem.,* 4: 581–585 (1993); and Buchner, et al., *Anal. Biochem.,* 205: 263–270 (1992) which are incorporated herein by reference.) Debinski et al., for example, describe the denaturation and reduction of inclusion body proteins in guanidine-DTE. The protein is then refolded in a redox buffer containing oxidized glutathione and L-arginine.

One of skill would recognize that modifications can be made to the IL-13 receptor targeted fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

Identification of Target Cells

It was a surprising discovery of the present invention that tumor cells overexpress IL-13 receptors. In particular, carcinoma tumor cells (e.g. renal carcinoma cells) overexpress IL-13 receptors at levels ranging from about 2100 sites/cell to greater than 150,000 sites per cell.

One of skill in the art will appreciate that identification of other cells that overexpress IL-13 receptors requires only routine screening using well-known methods. Typically this involves providing a labeled molecule that specifically binds to the IL-13 receptor. The cells in question are then contacted with this molecule and washed. Quantification of the amount of label remaining associated with the test cell provides a measure of the amount of IL-13 receptor (IL-13R) present on the surface of that cell.

In a preferred embodiment, IL-13 receptor may be quantified by measuring the binding of $^{125}$I-labeled IL-13 ($^{125}$I-IL-13) to the cell in question. Details of such a binding assay are provided in Example 1.

Pharmaceutical Compositions

The chimeric molecules of this invention are useful for parenteral, topical, oral, or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, capsules and lozenges. It is recognized that the fusion proteins and pharmaceutical compositions of this invention, when administered orally, must be protected from digestion. This is typically accomplished either by complexing the protein with a composition to render it resistant to acidic and enzymatic hydrolysis or by packaging the protein in an appropriately resistant carrier such as a liposome. Means of protecting proteins from digestion are well known in the art.

The pharmaceutical compositions of this invention are particularly useful for parenteral administration, such as intravenous administration or administration into a body cavity or lumen of an organ. The compositions for administration will commonly comprise a solution of the chimeric molecule dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington's Pharmaceutical Science*, 15th ed., Mack Publishing Company, Easton, Pa. (1980).

The compositions containing the present fusion proteins or a cocktail thereof (i.e., with other proteins) can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the proteins of this invention to effectively treat the patient.

Among various uses of the cytotoxic fusion proteins of the present invention are included a variety of disease conditions caused by specific human cells that may be eliminated by the toxic action of the protein. One preferred application is the treatment of cancer, such as by the use of an IL-13 receptor targeting molecule (e.g. IL-13 or anti-IL-13R antibody) attached to a cytotoxin.

Where the chimeric molecule comprises an IL-13 receptor targeting molecule attached to a ligand, ligand portion of the molecule is chosen according to the intended use. Proteins on the membranes of T cells that may serve as targets for the ligand includes CD2 (T11), CD3, CD4 and CD8. Proteins found predominantly on B cells that might serve as targets include CD10 (CALLA antigen), CD19 and CD20. CD45 is a possible target that occurs broadly on lymphoid cells. These and other possible target lymphocyte target molecules for the chimeric molecules bearing a ligand effector are described in *Leukocyte Typing III*, A. J. McMichael, ed., Oxford University Press (1987). Those skilled in the art will realize ligand effectors may be chosen that bind to receptors expressed on still other types of cells as described above, for example, membrane glycoproteins or ligand or hormone receptors such as epidermal growth factor receptor and the like.

Diagnostic Kits

In another embodiment, this invention provides for kits for the treatment of tumors or for the detection of cells overexpressing IL-13 receptors. Kits will typically comprise a chimeric molecule of the present invention (e.g. IL-13-label, IL-13-cytotoxin, IL-13-ligand, etc.). In addition the kits will typically include instructional materials disclosing means of use of chimeric molecule (e.g. as a cytotoxin, for detection of tumor cells, to augment an immune response, etc.). The kits may also include additional components to facilitate the particular application for which the kit is designed. Thus, for example, where a kit contains a chimeric molecule in which the effector molecule is a detectable label, the kit may additionally contain means of detecting the label (e.g. enzyme substrates for enzymatic labels, filter sets to detect fluorescent labels, appropriate secondary labels such as a sheep anti- mouse-HRP, or the like). The kits may additionally include buffers and other reagents routinely used for the practice of a particular method. Such kits and appropriate contents are well known to those of skill in the art.

EXAMPLES

The following examples are offered to illustrate, but not to limit the claimed invention. All references cited in the foregoing discussion and the following examples are incorporated herein by reference.

Example 1

Identification of Cell that Overexpress IL-13

Recombinant human IL-4 and IL-13 were labeled with $^{125}$I (Amersham Research Products, Arlington Heights, Ill., U.S.A.) by using the IODO-GEN reagent (Pierce, Rockford, Ill., U.S.A.) according to the manufacturer's instructions. The specific activity of the radiolabeled cytokines was estimated to range from 20–100 µCi/µg protein. For binding experiments, typically, $1 \times 10^6$ renal cell carcinoma (RCC) tumor cells were incubated at 4° C. for 2 hours with $^{125}$I-IL-13 (100 pM) with or without increasing concentrations (up to 500 nM) of unlabeled IL-13. In some experiments, IL-13R expression was examined as previously described (Obiri et al. *J. Clin. Invest.*, 91: 88–93 (1993))). The data were analyzed with the LIGAND program (Munson et al. *Anal. Biochem.*, 107: 220–239 (1980)) to determine receptor number and binding affinity.

Four human renal cell carcinoma (RCC) cell lines (WS-RCC, HL-RCC, PM-RCC, and MA-RCC) bound $^{125}$I-IL-13 specifically and the density of IL-13 R varied from 2100 sites per cell in WS-RCC cells to 150,000 sites per cell in HL-RCC cells (Table 1). The represents an increase in IL-13 receptor expression ranging from 15 to about 500 fold as compared to normal immune cells. In contrast, IL-4 receptors overexpressed on cancers have been reported at concentrations as high as 4000 sites per cell. Scatchard analyses (Scatchard, *Ann. N.Y. Acad. Sci.*, 51: 660–663 (1949)) revealed that only one affinity class of receptors was expressed on each cell line. The binding affinities (Kd) ranged between 100 pM to 400 pM in three RCC cell lines while HL-RCC cells expressed lower affinity receptors (Kd~3 nM).

Although IL-13 responsiveness has previously been reported in human monocytes, B cells and pre-myeloid (TF-1) cells (see, e.g. de Waal Malefyt, et al. *J. Immunol.*, 151: 6370–6381 (1993), de Waal Malefyt, et al. *J. Immunol.*, 144: 629–633 (1993)), little was known about IL-13R structure or its binding characteristics in these, or any other cells. The present data show that freshly isolated human monocytes, EBV-transformed B cell line and TF-1 cell line express very few IL-13 binding sites (100–300/cell) compared to human RCC cells (Table 1). On the other hand, no binding of $^{125}$I-IL-13 was observed on H9 T cells, LAK cells and resting or PHA activated PBL. This is compatible with the fact that IL-13 responsiveness has not been observed in T lymphocytes (Punnonen et al., *Proc. Natl. Acad. Sci. USA*, 90: 3730–3734 (1993).

TABLE 1

Expression of IL-13 receptor by human cells.

| Cell Types | IL-13 Binding Sites/cell[a] Mean ± SD | Kd(nM) Mean ± SD |
|---|---|---|
| Renal Cell Carcinoma (RCC) | | |
| 1. WS-RCC | 2,090 ± 367 (5) | 0.247 ± 0.12 (3)[b] |
| 2. MA-RCC | 5,013 ± 1.347 (5) | 0.128 ± 0.05 (2) |
| 3. PM-RCC | 26,500 ± 5.000 (2) | 0.394 ± 0.26 (2) |
| 4. HL-RCC | 150,000 ± 15.00 (3) | 3.1 ± 0.7 (2) |
| B Lymphocytes | | |
| 1. DH (EBV-transformed B cell line) | 303 ± 90 (4) | —[d] |
| 2. RAJI (Burkitt's lymphoma) | UD[c] | — |
| Monocytes/Premyeloid cells[e] | | |
| 1. Peripheral blood monocytes | 124 | — |
| 2. U937 (premonocytic | UD | — |
| 3. TF1.J61 (premyeloid) | 130 ± 1 (2) | — |
| T Lymphocytes/LAK cells[f] | | |
| 1. PHA-activated PBL | <30 | — |
| 2. MOLT-4 (T-cell leukemia) | UD | — |
| 3. LAK cells | UD | — |

[a]IL-13 binding sites/cell were determined as described in Example 1.
[b](n) = number of experiments used to calculate mean ± standard deviation.
[c]UC = undetectable
[d]The Kd could not be reliably calculated because of low binding of $^{125}$I-IL-13
[e]The peripheral blood derived monocytes (>90% purity) were isolated by ficoll-hypaque density gradient followed by ellutriation from a leukopac obtained from normal donor.
[f]LAK cells and activated T-lymphocytes were generated by the culture of donor PBLs (106/ml) with IL-2 (500 Units/ml) for 3 days or PHA (10 µg/ml) for 3–4 days respectively.

Example 2

IL-13 and IL-4 Bind to Different Receptors

Recently, it was proposed that the IL-2R$\gamma_c$ receptor subunit is associated with IL-13R (see, e.g., Russell et al. *Science* 262: 1880–1883 (1993); Kondo et al. *Science*, 262: 1874–1877 (1993); Noguchi et al. *Science*, 262: 1877–1880 (1993); Kondo et al. *Science* 263: 1453–1454 (1994); Giri et al. *EMBO J.* 13: 282–2830 (1994))) and IL-13R may share a common component with IL-4R (Zurawski et al. *EMBO J.* 12: 2663–2670 (1993); Aversa et al. *J. Exp. Med.* 178: 2213–2218 (1993)). To directly address these possibilities, radio-ligand binding experiments were performed, as described in Example 1, on HL-RCC and WS-RCC cells using $^{125}$I-IL-4 or $^{125}$I-IL-13 in the presence or absence of excess of either cytokine.

Unlabeled IL-4 more efficiently inhibited $^{125}$I-IL-4 from binding to RCC cells (84%, and 72% displacement of total binding in WS-RCC and HL-RCC, respectively) than IL-13 which also displaced $^{125}$I-IL-4 binding to these cells (61% of total binding in WS-RCC and 51% in HL-RCC) under similar conditions. On the other hand, while $^{125}$I-IL-13 binding was effectively displaced by IL-13 (about 85% of total in both cell types), it was only minimally displaced by IL-4 (12% of total displacement in WS-RCC, and 7% in HL-RCC). These results indicate that IL-4 and IL-13 both interact with each other's receptors, however, the interaction is not identical since IL-4 inhibition of $^{125}$I-IL-13 binding was weak and IL-13 inhibition of $^{125}$I-IL-4 binding was not complete. These results agree with previous observations in which IL-13 was found to compete with IL-4 binding on TF-1 cells (Zurawski et al., *EMBO J.* 12: 2663–2670 (1993)). However, in that report the converse experiment was not done. Here, the data show that even though IL-13 competed for IL-4 binding, IL-4 did not compete for IL-13 binding.

The competition by IL-13 for IL-4 binding sites on lymphoid MLA 144 cells and RAJI cell lines was also investigated. These cells were incubated with radiolabled IL-4 with or without excess unlabeled IL-4 or IL-13. Excess unlabeled IL-4 effectively displaced labeled $^{125}$I-IL-4 bound to MLA 144 and RAJI cells, while excess IL-13 could not compete this binding. This observation is at variance to that seen with RCC cells in which IL-13 competed for IL-4 binding. The inability of IL-13 to compete for $^{125}$I-IL-4 binding to MLA 144 is consistent with the observation that IL-13 did not bind to peripheral blood T (or MLA 144) cells.

Example 3

Subunit Structure of IL-13 and IL-4 Receptors

The subunit structure of IL-13R on RCC cells was investigated by crosslinking studies. Cells (5×10$^6$) were labeled with $^{125}$I-IL-13 or $^{125}$I-IL-4 in the presence or absence of excess IL-13 or IL-4 for 2 h at 4° C. The bound ligand was cross-linked to its receptor with disuccinimidyl subcrate (DSS) (Pierce, Rockford, Ill., U.S.A.) at a final concentration of 2 mM for 30 min. Cells were lysed in a buffer containing 1% Triton X-100, 1 mM phenylmethylsulfonyl fluoride, 0.02 mM leupeptin, 5.0 µM trypsin inhibitor, 10 mM benzamidine HCl, 1 mM phenanthroline iodoacetamide, 50 mM amino caproic acid, 10 µg/ml pepstatin, and 10 µg/ml aprotinin. The cell lysates were cleared by boiling in buffer containing 2-mercaptoethanol and analyzed by electrophoresis through 8% SDS/polyacrylamide gel. The gel was subsequently dried and autoradiographed. In some experiments, the receptor/ligand complex was immunoprecipitated from the lysate overnight at 4° C. by incubating with protein A sepharose beads that had been pre-incubated with P7 anti hIL-4R or anti-$\gamma_c$ antibody and analyzed as above.

The labeled $^{125}$I-IL-13 cross-linked to one major protein on all four RCC cell lines and the complex migrated as a single broad band ranging between 68 and 80 kDa. A single band was also observed on human pre-myeloid TF-1.J61 cells only after much longer exposure of the gel. After subtracting the molecular mass of IL-13 (12 kDa), the size of IL-13 binding protein was estimated at 56 to 68 kDa. The $^{125}$I-IL-13 cross-linked band was not observed when the crosslinking was performed in the presence of 200-fold molar excess of IL-13. In addition to the major band, a faint band of approximately 45 kDa was also observed in HL-RCC and PM-RCC but not on MA-RCC cells. This band appeared to be specifically associated with IL-13R because unlabeled IL-13 competed for the binding of $^{125}$I-IL-13. This band could represent an IL-13R associated protein or a proteolytic fragment of the larger band. In contrast to the displacement of $^{125}$I-IL-13 binding by unlabeled IL-13, an excess of unlabeled IL-4 did not prevent the appearance of IL-13 R band in RCC cell lines. IL-13 on the other hand competed for $^{125}$I-IL-4 binding to both major proteins on WS-RCC cells. It is of interest that $^{125}$I-IL-13-cross-linked protein was slightly larger in size in TF-1.J61, WS-RCC, PM-RCC, and HL-RCC cell lines compared to that seen in MA-RCC. Post-translational modifications, such as glycosylation or phosphorylation, may account for this difference.

Example 4

Construction of an IL-13-PE Fusion Protein

Construction of a Plasmid Encoding IL-13-PE38QQR

To construct the chimeric toxin a coding region of the human interleukin 13 (hIL-13) gene (plasmid JFE14-SRα) (Minty et al., *Nature*, 362: 248 (1993), McKenzie et al. *Proc. Natl. Acad. Sci. U.S.A.*, 90: 3735 (1987) which are incorporated herein by reference) was fused to a gene encoding PE38QQR, a mutated form of PE, thereby producing a construct (phuIL-13-Tx) encoding the chimeric molecule. Specifically, a DNA encoding human IL-13 was PCR-amplified from plasmid JFE14-SRα. New sites were introduced for the restriction endonucleases NdeI and Hind III at the 5' and 3' ends of the hIL-13 gene, respectively by PCR using a sense primer that incorporated the NdeI site and an antisense primer that incorporated the HindIII site.

The NdeI/HindIII fragment containing encoding hIL-13 was subcloned into a vector obtained by digestion of plasmid pWDMH4-38QQR (Debinski et al. *Int. J. Cancer* 58: 744–748 (1994)) or plasmid pSGC242FdN1 (Debinski et al. *Clin. Res.* 42: 251A, (abstr.) (1994) with NdeI and HindIII, to produce plasmid phuIL-13-Tx. The 5' end of the gene fusion was sequenced and showed the correct DNA of hIL-13.

Human interleukin 4 (hIL-4) was cloned into an expression vector in a similar way to hIL-13 using plasmid pWDMH4 (Debinski et al. *J. Biol. Chem.* 268: 14065–14070 (1993)) as a template for PCR amplification. Recombinant proteins were expressed in *E. coli* BL21 (λDE3) under control of the T7 late promoter (Id.). In addition to the T7 bacteriophage late promoter, the plasmids also carried a T7 transcription terminator at the end of the open reading frame of the protein, an f1 origin of replication and gene for ampicillin resistance (Debinski et al. *J. Clin. Invest.* 90: 405–411 (1992)). The plasmids were amplified in *E. coli* (HB101 or DH5α high efficiency transformation) (BRL) and DNA was extracted using Qiagen kits (Chatsworth, Calif., U.S.A.).

Expression and purification of recombinant proteins

*E. coli* BL21 (λDE3) cells were transformed with plasmids of interest and cultured in 1.0 liter of Super broth. Expressed recombinant human IL-13 and human IL-13-PE38QQR were localized in inclusion bodies. The recombinant proteins were isolated from the inclusion bodies as described by Debinski et al., *J. Biol. Chem.* 268: 14065–14070 (1993), which is incorporated herein by reference. After dialysis, the renatured protein of human IL-13-PE38QQR was purified on Q-Sepharose Fast Flow and by size exclusion chromatography on Sephacryl S-200HR (Pharmacia, Piscataway, N.J., U.S.A.) The initial step of hIL-13 or hIL-4 purification was conducted on SP-Sepharose Fast Flow (Pharmacia).

Protein concentration was determined by the Bradford assay (Pierce "Plus", Rockford, Ill., U.S.A.) using BSA as a standard.

Human IL-13 and IL-13-PE38QQR were expressed at high levels in bacteria as seen in SDS-PAGE analysis of the total cell extract. After initial purification on SP-Sepharose (hIL-13) or Q-Sepharose (hIL-13-PE38QQR) the renatured recombinant proteins were applied onto a Sephacryl S-200 HR Pharmacia column. Human IL-13 and hIL-13-PE38QQR appeared as single entities demonstrating the very high purity of the final products. The chimefie toxin migrated within somewhat lower than expected for 50 kDa protein M$_r$ range which may be related to the hydrophobicity of the molecule. The biologic activity of the rhIL-13 was exactly the same as commercially obtained hIL-13.

Example 4

The Activity of an IL-13-PE Fusion Protein on Human Carcinoma Cells

Cytotoxic Activity of hIL-13-PE38QQR

The cytotoxic activity of chimeric toxins, such as hIL-13-PE38QQR, were tested by measuring inhibition of protein synthesis. Protein synthesis was assayed by plating about $1 \times 10^4$ cells per in a 24-well tissue culture plate in 1 ml of medium. Various concentrations of the chimeric toxins were added 20–28 h following cell plating. After 20 h incubation with chimeric toxins, [$^3$H]-leucine was added to cells for 4 h, and the cell-associated radioactivity was measured. For blocking studies, rhIL-2, 4 or 13 was added to cells for 30 min before the chimeric toxin addition. Data were obtained from the average of duplicates and the assays were repeated several times.

Several established cancer cell lines were tested to determine if hIL-13 PE38QQR is cytotoxic to them. In particular, cancers derived from colon, skin and stomach were examined. The cancer cells were sensitive to hIL-13-PE38QQR with ID$_{50}$s ranging from less than 1 ng/ml to 300 ng/ml (20 pM to 6.0 nM) (ID$_{50}$ indicates the concentration of the chimeric toxin at which the protein synthesis fell by 50% when compared to the sham-treated cells). A colon adenocarcinoma cell line, Colo201, was very responsive with an IC$_{50}$ of 1 ng/ml. A431 epidermoid carcinoma cells were also very sensitive to the action of hIL-13-toxin; the ID$_{50}$ for hIL-13-PE38QQR ranged from 6 10 ng/ml. A gastric carcinoma CRL1739 cell line responded moderately to the hIL-13-toxin with an ID$_{50}$ of 50 ng/ml. Another colon carcinoma cell line, Colo205, had a poorer response with an ID$_{50}$ of 300 ng/ml.

The cytotoxic action of hIL-13-PE38QQR was specific as it was blocked by a 10-fold excess of hIL-13 on all cells. These data suggest that a spectrum of human cancer cells possess hIL-13 binding sites and such cells are sensitive to hIL-13-PE38QQR chimeric toxin.

Because the hIL-13R has been suggested to share the $\lambda_c$ subunit of the IL-2R (Russell et al. *Science* 262: 1880–1883 (1993)), the specificity of hIL-13-PE38QQR action on A431 and CRL1739 cells, the two cell lines with different sensitivities to the chimeric toxin was further explored. The cells were treated with hIL-13-PE38QQR with or without rhIL-2 at a concentration of 1.0 µg/ml or 10 µg/ml. The rhIL-2 did not have any blocking action on hIL-13-PE38QQR on the two cell lines, even at 10,000 fold molar excess over the chimeric toxin. These results indicate that the cell killing by the hIL-13-toxin is independent of the presence of hIL-2.

IL-4, unlike IL-2, blocks the action of IL-13-PE38QQR

Native hIL-4 was added to cells which were then treated with hIL-13 PE38QQR. Unexpectedly, it was found that hIL-4 inhibited the cytotoxic activity of the hIL-13-toxin. This phenomenon was seen on all the tested cell lines, including Colo201, A431 and CRL1739. To investigate the possibility that hIL-13 and hIL-4 may compete for the same binding site, the cells were also treated with the hIL-4-based recombinant toxin, hIL-4-PE38QQR (Debinski et al. *Int. J. Cancer* 8: 74–748 (1994)). The cytotoxic action of hIL-4-PE38QQR had already been shown to be blocked by an excess of hIL-4 but not of hIL-2 (Id.). In the present experiment hIL-13 potently blocked the cytotoxic activity of hIL-4-PE38QQR. Also, the action of another hIL-4-based chimeric toxin, hIL-4-PE4E (Debinski et al. *J. Biol. Chem.* 268: 14065–14070 (1993)), was blocked by an excess of hIL-13 on Colo201 and A431 cells. Thus, the cytotoxicity of hIL-13-PE38QQR is blocked by an excess of hIL-13 or hIL-4, and the cytotoxic action of hIL-4-PE38QQR is also blocked by the same two growth factors. However, IL-2 does not block the action of either chimeric toxin. These results strongly suggest that hIL-4 and hIL-13 have affinities for a common binding site.

This conclusion was supported by the observation of one cytokine blocking the effect of a mixture of the two chimeric toxins. When A431 cells were incubated with both hIL-3- and hIL-4-PE38QQR chimeric toxins concomitantly the cytotoxic action was preserved and additive effect was observed as expected. An excess of hIL-13 efficiently blocked the action of a mixture of the two chimeric toxins. Moreover, neither hIL-13 nor hIL-4 blocked cell killing by another mixture composed of hIL-13-PE38QQR and TGFα-PE40, a chimeric toxin which targets the EGFR (TGFα-based chimeric toxin, TGFα-PE40) (Siegall et al. *FASEB J.* 3, 2647–2652 (1992)). The same was observed on Colo201 cells.

Reciprocal Blocking of Chimeric Toxins by IL-13 and IL-4 is due to competition for binding sites The binding ability of human IL-13 was compared to human IL-4-PE38QQR in competitive binding assays. Recombinant hIL-4-PE38QQR was labeled with $^{125}$I using the lactoperoxidase method as described by Debinski et al., *J. Clin. Invest.* 90, 405–411 (1992). Binding assays were performed by a standard saturation and displacement curves analysis. A431 epidermoid carcinoma cells were seeded at $10^5$ cells per well in a 24-well tissue culture plates at 24 h before the experiment. The plates were placed on ice and cells were washed with ice-cold PBS without Ca++, Mg++ in 0.2% BSA, as described (Id.). Increasing concentrations of hIL-13 or hIL-4-PE38QQR were added to cells and incubated 30 min prior to the addition of fixed amount of $^{125}$I-hIL-4-PE38QQR (specific activity 6.2 µCi/µg protein) for 2 to 3 h. After incubation, the cells were washed twice and lysed with 0.1N NaOH, and the radioactivity was counted in a γ-counter.

Human IL-4-PE38QQR competed for the binding of $^{125}$I-hIL-4-PE38QQR to A431 cells with an apparent $ID_{50}$ of $4\times10^{-8}$M. In addition, hIL-13 also competed for the $^{125}$I-hIL-4-PE38QQR binding site with a comparable potency to that exhibited by the chimeric protein. More extensive binding studies have shown that hIL-13 also competes for hIL-4 binding sites on human renal carcinoma cell lines.

The possibility of an influence of hIL-13 or hIL-4 on the process of receptor-mediated endocytosis and post-binding PE cellular toxicity steps was excluded by adding to cells: (i) native PE (PE binds to the $\alpha_2$-macroglobulin receptor), (ii) TGFα-PE40, and (iii) a recombinant immunotoxin C242rF(ab)-PE38QQR (Debinski et al. *Clin. Res.* 42, 251A, (Abstr.) (1994)). C242rF(ab)-PE38QQR binds a tumor-associated antigen that is a sialylated glycoprotein (Debinski et al. *J. Clin. Invest.* 90: 405–411 (1992)). The expected cytotoxic actions of these recombinant toxins were observed and neither hIL-13 nor hIL-4 blocked these actions on A431 and Colo205 cells.

hIL-4 and hIL-13 compete for a common binding site on carcinoma cell but evoke different biological effects Even though hIL-13 and hIL-4 compete for a common binding site, they induce different cellular effects. Protein synthesis was inhibited in A431 epidermoid carcinoma cells in a dose-dependent manner by hIL-4 alone, or by a ADP-ribosylation deficient chimeric toxin containing hIL-4 (Debinski et al. *Int. J. Cancer* 58: 744–748 (1994)). This effect of hIL-4 or enzymatically deficient chimeric toxin can be best seen with a prolonged time of incubation ($\geq 24$ h) and requires concentrations of hIL-4 many fold higher than that of the active chimeric toxin in order to cause a substantial decrease in tritium incorporation. However, when A431 cells were treated with various concentrations of hIL-13, no inhibition (or stimulation) of protein synthesis was observed, even at concentrations as high as 10 µg/ml of hIL-13 for a 72 h incubation. The same lack of response to hIL-13 was found on renal cell carcinoma cells PM-RCC. Thus, while hIL-13 and hIL-4 may possess a common binding site, they appear to transduce differently in carcinoma cells expressing this common site, such as A431 and PM-RCC cells.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method for specifically delivering an effector molecule to a solid tumor cell bearing an IL-13 receptor, said method comprising:

providing a chimeric molecule comprising said effector molecule attached to a targeting molecule selected from the group consisting of an IL-13, and an anti-IL-13 receptor antibody; and contacting said chimeric molecule with said tumor cell to specifically bind said chimeric molecule to said tumor cell.

2. The method of claim 1, wherein said targeting molecule is IL-13.

3. The method of claim 1, wherein said tumor is a carcinoma.

4. The method of claim 1, wherein said effector molecule is selected from the group consisting of a cytotoxin, a label, a radionuclide, a drug, a liposome, a ligand, and an antibody.

5. The method of claim 4, wherein said effector molecule is a Pseudomonas exotoxin.

6. The method of claim 5, wherein chimeric molecule is a fusion protein.

7. The method of claim 6, wherein said fusion protein is IL-13-PE38QQR.

8. The method of claim 1, wherein said effector molecule is a detectable label and said method further comprises detecting said label and thereby detecting said tumor cell.

9. The method of claim 8, wherein said detectable label is selected from the group consisting of a radiolabel, an enzyme, a colorimetric label, a fluorescent label, and a magnetic bead.

10. The method of claim 8, wherein said label is a fluorescent label.

11. The method of claim 8, wherein said detecting is by scintillography.

12. The method of claim 8, wherein said tumor cell is a carcinoma cell.

13. The method of claim 11, wherein said carcinoma is selected from the group consisting of colon carcinoma, skin carcinoma, and gastric carcinoma.

14. A method for impairing growth of a solid tumor cell bearing an IL-13 receptor, said method comprising contacting said tumor cell with a chimeric molecule comprising:

a targeting molecule selected from the group consisting of an IL-13, and an anti-IL-13 receptor antibody; and an effector molecule selected from the group consisting of a Pseudomonas exotoxin, a Diphtheria toxin, and a radionuclide, wherein said effector molecule may be linked to the targeting molecule by a linker consisting of a ligand or an antibody; and wherein said contacting specifically binds said chimeric molecule to said tumor cell.

15. The method of claim 14, wherein said targeting molecule is a human IL-13.

16. The method of claim 15, wherein said effector molecule is a Pseudomonas exotoxin or a Diphtheria toxin.

17. The method of claim 16, wherein chimeric molecule is a single-chain fusion protein.

18. The method of claim 17, wherein said effector molecule is a Pseudomonas exotoxin.

19. The method of claim 18, wherein said Pseudomonas exotoxin is PE38QQR.

20. The method of claim 15, wherein said tumor cell growth is tumor cell growth in a human.

21. The method of claim 20, wherein said contacting comprises administering said chimeric molecule to the human intravenously, into a body cavity, or into a lumen or an organ.

* * * * *